United States Patent [19]

Callander

[11] Patent Number: 5,202,495

[45] Date of Patent: Apr. 13, 1993

[54] CHEMICAL PROCESS

[76] Inventor: Sidney E. Callander, Beecham Pharmaceuticals, Clarendon Road, Worthing, West Sussex BN14 8QH, England

[21] Appl. No.: 595,786

[22] Filed: Oct. 10, 1990

Related U.S. Application Data

[63] Continuation-in-part of Ser. No. 374,592, Jun. 29, 1989, abandoned, which is a continuation of Ser. No. 172,714, Mar. 24, 1988, abandoned.

[30] Foreign Application Priority Data

Mar. 26, 1987 [GB] United Kingdom ............... 8707200

[51] Int. Cl.$^5$ .............................................. C07C 45/62
[52] U.S. Cl. .................................... 568/315; 568/313
[58] Field of Search ...................... 568/313, 318, 315

[56] References Cited

U.S. PATENT DOCUMENTS

| 3,708,540 | 1/1973 | Vokotani et al. | 568/313 |
| 4,061,779 | 12/1977 | Lake et al. | 568/313 |
| 4,221,741 | 9/1980 | Gaster | 568/318 |
| 4,221,829 | 4/1981 | Horner et al. | 568/318 |
| 4,270,004 | 5/1981 | Rose et al. | 568/314 |
| 4,521,629 | 6/1985 | Cortese et al. | 568/313 |

FOREIGN PATENT DOCUMENTS 288144 10/1988 European Pat. Off. ............ 568/388

OTHER PUBLICATIONS

Organic Reactions, Jones, vol. 15, pp. 246-249 (1967).
Knoevenagel et al, Ber., vol. 37, pp. 4490-4502 (1904).
Martin et al., J.A.C.S. vol. 80, pp. 5852-5856 (1958).

*Primary Examiner*—James H. Reamer
*Attorney, Agent, or Firm*—Hopgood, Calimafde, Kalil, Blaustein & Judlowe

[57] ABSTRACT

A process for the preparation of the compound of formula (I), 3-(6'methoxy-2'-naphthylmethyl)-2,4-pentanedione,

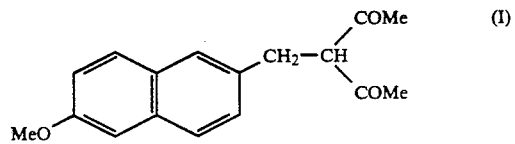

comprises the calalytic hydrogenation of a compound of formula (II):

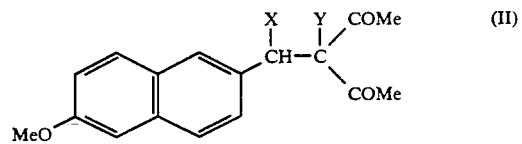

7 Claims, No Drawings

CHEMICAL PROCESS

This application is a continuation-in-part of application Ser. No. 374,592, filed Jun. 29, 1989, now abandoned which is a continuation of application Ser. No. 172,714, filed Mar. 24, 1988, now abandoned.

This invention relates to a novel process for preparing an intermediate compound useful for preparing 4-(6'-methoxy-2'-naphthyl)butan-2-one.

U.S. Pat. No. 4,061,779 describes 4-(6'-methoxy-2'-naphthyl)butan-2-one (nabumetone) and its use in the treatment of rheumatic and arthritic conditions. A number of processes for preparing the compound are also described, one of which proceeds via a saturated diketone intermediate of formula (I), although there is no specific disclosure of this intermediate, nor of its structure. In the above patent, the compound of formula (I) is produced in a reaction medium comprising acetylacetone and potassium carbonate (Example 22 of the patent), but the compound is not disclosed as being isolated from this medium.

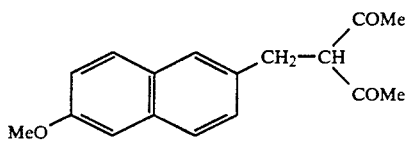

A further process for the preparation of the saturated diketone intermediate of formula (I) has now been discovered which is characterised by the reduction of a product formed by the condensation of 6-methoxy-2-naphthaldehyde with acetylacetone.

Accordingly, the present invention provides a process for the preparation of the compound of formula (I), 3-(6'-methoxy-2'-naphthylmethy)-2,4-pentanedione, which comprises the reduction of a compound of formula (II):

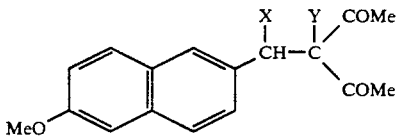

wherein X is a hydroxyl group and Y is hydrogen or X and Y together form a bond.

The compound of formula (I) thereby produced may then be de-acetylated under basic conditions to produce nabumetone.

The compound of formula (II) may itself be produced by the condensation of 6-methoxy-2-naphthaldehyde with acetylacetone, preferably in an inert solvent or solvent mixture. A suitable solvent is one which forms an azeotrope with water.

The condensation reaction may be carried out at reduced, normal or elevated pressures and at reduced, ambient or elevated temperatures. Typically, the reaction may be carried out at a pressure of from $10^3$ to $10^6$ $Nm^{-2}$, and at a temperature of from 15° C. or above. It is believed that the condensation reaction proceeds via the intermediate compound of formula (II) in which X is a hydroxyl group and Y is hydrogen, and that this intermediate spontaneously eliminates water to produce the α,β-unsaturated diketone intermediate of formula (II) in which X and Y together form a bond.

In a preferred aspect, the condensation of 6-methoxy-2-naphthaldehyde with acetylacetone is carried out in toluene at a reduced pressure of about $7 \times 10^3 Nm^{-2}$ at the reflux temperature of the solvent, with azeotropic removal of water, to give the α,β-unsaturated diketone intermediate compound of formula (II) which is isolated by cooling and filtration.

The reduction of the compound of formula (II) may be carried out by catalytic hydrogenation, employing a low, medium or high pressure of hydrogen, for example in the range $0.1 \times 10^5$ to $10^6$ $Nm^{-2}$. In general it is preferred to use a hydrogen pressure in the range $0.9 \times 10^5$ to $1.5 \times 10^5$ $Nm^{-2}$, for example atmospheric pressure.

The hydrogenation will be carried out in the presence of a catalyst, preferably a noble metal catalyst such as palladium. Suitable forms of palladium catalysts include palladium on charcoal, palladium on barium sulphate or palladium on calcium carbonate. Palladium on charcoal is particularly preferred.

The hydrogenation reaction is preferably carried out in an inert solvent, such as a lower alcohol, weak acid, ester, hydrocarbon (such as toluene), halohydrocarbon or ketonic solvent, or a suitable mixture of solvents. The reaction may take place in an aqueous medium. Preferably the reaction is carried out in ethyl acetate.

The reaction may be performed at an ambient or elevated temperature, for example 20° C. to 100° C. and more suitably 45° C. to 65° C., preferably 60° C.

Once the reaction is over (for example as judged by hplc, tlc or cessation of hydrogen uptake) the desired compound may be obtained by filtering off the catalyst and removal of the solvent, for example by evaporation under reduced pressure.

If desired the compound may be purified by recrystallisation or directly de-acetylated to produce nabumetone.

Compounds of formula (II) are novel and form an aspect of the present invention. The isolated compound of formula (I) is also novel and forms a further aspect of the present invention.

The following examples illustrate the invention.

EXAMPLE 1

3-(6'Methoxy-2'-naphthylmethylene)-2,4-pentanedione

Piperidine (6.32 g), acetic acid (4.52 g), acetylacetone (118 g) and 6-methoxy-2-naphthaldehyde (200 g) were added to toluene (500 ml) in a glass reactor equipped with a stirrer and a Dean and Stark reflux system.

The pressure was reduced to ca $7 \times 10^3$ $Nm^{-2}$, and heating applied so that reflux started at ca 40° C. Water liberated from the reaction was removed continuously, and after ca 5 hours, the reaction mixture was cooled to 0°–5° C. The crystalline product was isolated by filtration after a further 2 hours, and dried at 45° C.

| | |
|---|---|
| Yield: | 267.3 g |
| Assay: | 99.1% |
| Activity Yield: | 93.7% |
| Melting Point: | 121–2° C. |

The structure of the product was confirmed by proton NMR, as follows:

| Line Position | Protons | Assignment |
| --- | --- | --- |
| 2.35 ppm | 3 | —COCH$_3$ |
| 2.45 ppm | 3 | —COCH$_3$ |
| 3.9 ppm | 3 | —OCH$_3$ |

EXAMPLE 2

3-(6'-Methoxy-2'-naphthylmethyl)-2,4-pentanedione 3-(6'-Methoxy-2'-naphthylmethylene)-2,4-pentanedione (50 g) was added to ethyl acetate (250 ml) in a glass reactor fitted with a reflux condenser, a gas inlet tube, and stirrer.

The mixture was heated to ca 60° C. while purging with nitrogen, and the catalyst (10% palladium on carbon, 0.8 g) was added as a slurry in ethyl acetate (25 ml).

The nitrogen flow was stopped and hydrogen was passed through the hot solution, with vigorous stirring, for ca 1 hour. The vessel was then purged with nitrogen while cooling the mixture to ca 30° C., and the catalyst was removed by filtration.

The ethyl acetate was distilled off under reduced pressure, and the oily residue was treated with isopropyl ether. The resulting white solid was isolated and dried at 45° C. Yield 50 g.

Alternatively, the filtrate was concentrated, then cooled to allow crystallisation of the material. (M.p. 75°–7° C.).

The structure of the product was confirmed by proton NMR, as follows:

| Line Position | Protons | Assignment |
| --- | --- | --- |
| 2.13 ppm | 6 | —COCH$_3$ |
| 3.9 ppm | 3 | —OCH$_3$ |

I claim:

1. A process for the preparation of 3-(6'-methoxy-2-'-naphthylmethyl)-2,4-pentanedione which comprises condensing 6-methyoxy-2-naphthaldehyde with acetylacetone in an inert solvent at a temperature of from about 15° C. to about 100° C. to form 3-(6'-methoxy-2'-naphthylmethylene)-2,4-pentanedione and subjecting this compound to catalytic hydrogenation in an inert solvent to form 3-(6'-methoxy-2'-naphthylmethyl)-2,4-pentanedione.

2. A process according to claim 1, in which said catalytic hydrogenation is accomplished by using hydrogen at a pressure of from $0.1 \times 10^5$ to $10^6$ Nm$^{-2}$.

3. A process according to claim 1 in which the catalyst comprises palladium.

4. A process according to claim 1 in which the condensation reaction is carried out at a pressure of from $10^3$ to $10^6$ Nm$^{-2}$ and a temperature of from $-5°$ to $100°$ C.

5. A process according to claim 4 in which the catalyst comprises palladium.

6. A process according to claim 2 in which the catalyst comprises palladium.

7. A process according to claim 1 which further comprises de-acetylating 3-(6'-methoxy-2'-naphthylmethyl)-2,4-pentanedione to form 4-(6'-methoxy-2'naphthyl)butan-2-one.

* * * * *